United States Patent [19]

Burpitt et al.

[11] 3,969,372

[45] July 13, 1976

[54] 2,3-DIHYDRO-3,3-DIMETHYL-2,5-BENZOFURANDIOL FROM ISOBUTYRALDEHYDE AND BENZOQUINONE

[75] Inventors: Robert D. Burpitt; David M. Pond; Mary E. Dickerson, all of Kingsport, Tenn.

[73] Assignee: Eastman Kodak Company, Rochester, N.Y.

[22] Filed: June 2, 1975

[21] Appl. No.: 583,339

[52] U.S. Cl............................................. 260/346.2 R
[51] Int. Cl.² .................................... C07D 307/83
[58] Field of Search ........................... 260/346.2 R

[56] References Cited
UNITED STATES PATENTS 3,285,937  11/1966  Brannock et al............. 260/346.2 R

*Primary Examiner*—Natalie Trousof
*Assistant Examiner*—Bernard Dentz
*Attorney, Agent, or Firm*—Elliott Stern; Daniel B. Reece, III

[57] ABSTRACT

This invention relates to a process involving the reaction of a quinone with a carbonyl compound in the presence of a basic catalyst to produce 2,3-dihydro-2,5-benzofurandiols. These compounds are useful intermediates in the synthesis of herbicides and plant growth regulants.

3 Claims, No Drawings

2,3-DIHYDRO-3,3-DIMETHYL-2,5-BENZOFURAN-DIOL FROM ISOBUTYRALDEHYDE AND BENZOQUINONE

This invention relates to a process for preparing 2,3-dihydro-2,5-benzofurandiols, valuable intermediate in the synthesis of certain 2-organyloxy-2,3-dihydro-5-benzofuranyl esters of alkyl sulfonic acids which are useful as herbicides and as plant growth regulants. These compounds may also be used as fungicides, insecticides, and anthelmintics. U.S. Pat. No. 3,689,507 describes certain 5-benzofuranyl esters which are found to possess physiological activity, and particularly plant physiological activity. These compounds may be used as herbicides, and as plant growth regulants. The process disclosed in this patent has disadvantages in that the method shown for their preparation starts with expensive materials, requires a great number of operating steps, and gives poor yields.

We have found a novel process whereby these defects are remedied by providing an easy, novel process which is useful in the preparation of these 5-benzofuranyl esters.

It has been found that 2,3-dihydro-3,3-dimethyl-2,5-benzofurandiols can be prepared by a process which comprises reacting a benzoquinone with at least an equal molar amount of isobutyraldehyde at a temperature of from 20° to about 85°C. in the presence of a basic catalyst selected from tri-lower alkyl amines, tri-lower alkyl phosphines, alkali metal lower alkoxides, triethylene diamine, 1,5-diazabicyclo[4.3.0]non-5-ene, or quinuclidine. As used herein to describe a substituent containing an alkyl moiety, the term "lower" designates a carbon content of up to about 4 carbon atoms.

Examples of suitable basic catalysts are trimethylamine, triethylamine, tributylamine, trimethylphosphine, triethylphosphine, tributylphosphine, sodium methoxide, sodium ethoxide, sodium propoxide, potassium methoxide, potassium ethoxide, potassium butoxide, etc.

In a preferred embodiment of this invention, the catalyst is triethylamine. Another preferred basic catalyst which may be used according to this invention is triethylenediamine.

The reaction of this invention proceeds according to the following general equation:

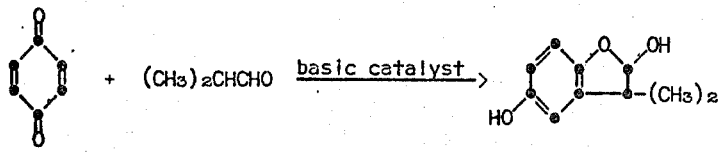

In the absence of basic catalyst, no reaction occurs at the reflux temperature of the isobutyraldehyde. If desired, the above reaction may be carried out at room temperature in excess isobutyraldehyde as solvent, or by the addition of a solution of p-benzoquinone in isobutyraldehyde to a refluxing solution of isobutyraldehyde containing a catalytic amount of the desired catalyst.

The reaction may also be carried out in various solvents such as ethanol, heptane, dimethylformamide, p-dioxane, etc. The preferred method, however, is the use of excess isobutyraldehyde as solvent at a reflux with triethylamine catalyst.

The reaction can be carried out in the presence of an inert atmosphere such as nitrogen or in the presence of air. An inert nitrogen atmosphere is preferred. Furthermore, the reaction may be carried out at atmospheric conditions.

The crude product, 2,3-dihydro-3,3-dimethyl-2,5-benzofurandiol, can easily be converted in two steps to the herbicide, 2-ethoxy-2,3-dihydro-3,3-dimethyl-5-benzofuranyl methanesulfonate, hereinafter referred to as Nortron, a product of Fisons Ltd. according to the following general equation:

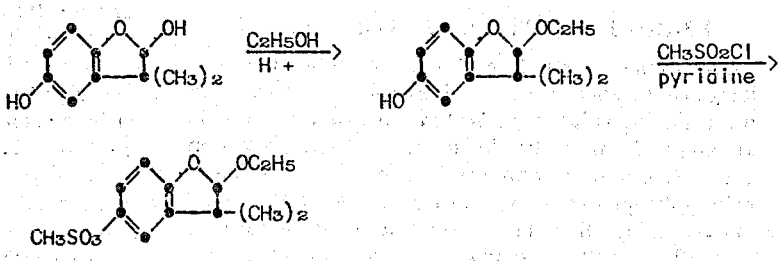

It should be emphasized that the compound prepared according to the novel process of this invention need not be isolated prior to reaction to the final herbicide.

The following examples further illustrate the invention.

EXAMPLE 1

Preparation of 2,3-Dihydro-3,3-dimethyl-2,5-benzofurandiol and Conversion to 2-Ethoxy-2,3-dihydro-3,3dimethyl-5-benzofuranyl Methanesulfonate (Nortron)

A solution of 21.6 g. (0.2 mole) of p-benzoquinone in 136 g. of isobutyraldehyde is added dropwise to a refluxing solution of 50g. of isobutyraldehyde containing 0.5 ml. of triethylamine under nitrogen. The excess isobutyraldehyde is stripped in vacuo to recover 160 g. The residue consists of 2,3-dihydro-3,3-dimethyl-2,5-benzofurandiol contaminated with a little hydroquinone. The presence of the benzofurandiol is indicated by comparison of spectra and tlc with authentic material as well as subsequent conversion to other known compounds. The crude mixture is dissolved in 250 ml. of ehtanol containing 1.5 g. of p-toluenesulfonic acid and refluxed for 1 hr. The solution is treated with solid potassium carbonate followed by filtration and removal of ethanol in vacuo. The viscous residue is dissolved in refluxing n-heptane and filtered to remove 5.1 g. of the insoluble hydroquinone. The heptane is removed from the filtrate by stripping in vacuo to give 35.1 g. of 2-ethoxy-2,3-dihydro-3,3-dimethyl-5-benzofuranol identified by comparison of tlc and ir spectra with authentic material. The crude ethoxy compound is dissolved in 100 ml. of pyridine and the solution cooled to 5–10°C. A total of 0.4 mole of methanesulfonyl chloride was added dropwise with stirring keeping temperature below 20°C. by a cooling bath. The reaction mixture is allowed to stand overnight at ambient temperature, then added to water and the product extracted with ether. The ether solution is washed five times with water followed by drying over $MgSO_4$. Evaporation of the solvent gives 43.7 g. (76%) of Nortron. The crude material is dissolved in $CHCl_3$ and is passed through a small bed of silica gel followed by removal of the $CHCl_3$ in vacuo to give 43.68 g. of product which is recrystallized from cyclohexane to give 31.7 g. (55%) of Nortron: m.p. 64–5°C. The ir spectrum is virtually identical to authentic Nortron.

EXAMPLE 2

2,3-Dihydro-3,3-dimethyl-2,5-benzofurandiol

A solution of 108 g. (1 mole) of p-benzoquinone in 1 liter of isobutyraldehyde is added dropwise with stirring to a refluxing solution of 500 ml. of isobutyraldehyde containing 5 ml. of triethylamine. The total addition and heating time is five hours. The excess isobutyraldehyde is stripped in vacuo leaving a crude oil that crystallized on standing. Trituration with cold chloroform gives 125 g. (70%) of product: m.p. 78°–81°C., nmr indicated the material to be 90–95% desired compound. A sample recrystallized from chloroform had a m.p. of 97°–99°C.

EXAMPLE 3

2-Ethoxy-2,3-dihydro-3,3-dimethyl-5-benzofuranyl Methanesulfonate (Nortron)

A solution of 108 g. (1 mole) of p-benzoquinone (dry, recrystallized from heptane) is 1 liter of isobutyraldehyde is added dropwise with stirring under nitrogen to a refluxing solution of 500 ml. of isobutyraldehyde containing 5 ml. of triethylamine. The total addition time is 2.75 hr. The excess isobutyraldehyde is removed in vacuo to give 1200 ml. of recovered material. The residue is treated with 1.5 liters of ethanol and 10 g. of p-toluenesulfonic acid and heated at reflux for 1 hr. Solid potassium carbonate is added and the solution allowed to stand overnight. The $K_2CO_3$ is filtered and the ethanol removed from the filtrate by distillation in vacuo. One liter of heptane is added and the solution filtered to remove salts and hydroquinone byproduct. The heptane is removed by distillation in vacuo. Tlc on the oil showed it to be largely 2-ethoxy-2,3-dihydro-3,3-dimethyl-5-benzofuranol along with some hydroquinone. A second treatment with hot heptane followed by filtration is carried out to remove hydroquinone. The residue from removal of heptane is dissolved in 500 ml. of pyridine and treated dropwise with stirring with a total of 160 g. (1.4 moles) of methanesulfonyl chloride at 5°–10°C. The resulting solution is added to ice water and the product is extracted with ether. The ether layer is washed with water to remove pyridine and dried over $MgSO_4$. The ether is removed and the residue recrystallized from cyclohexane to give 192.4 g. (67%) of Nortron: m.p. 60°–62°C. The ir and nmr spectra confirms the structure.

Although the invention has been described in considerable detail with particular reference to certain preferred embodiments thereof, it will be understood that variations and modifications can be effected within the spirit and scope of the invention.

We claim:

1. A method for preparing 2,3-dihydro-3,3-dimethyl-2,5-benzofurandiol which comprises reacting benzoquinone with at least an equal molar amount of isobutyraldehyde at a temperature of from about 20° to about 85°C. in the presence of a basic catalyst selected from tri-lower alkyl amines, tri-lower alkyl phosphines, alkali metal lower alkoxides, triethylenediamine, 1,5-diazabicyclo[4.3.0]non-5-ene, or quinuclidine.

2. The method of claim 1 wherein the catalyst is triethylamine.

3. The method of claim 2 wherein the reaction is carried out in an excess of isobutyraldehyde.

* * * * *